(12) United States Patent
Nakajima et al.

(10) Patent No.: US 10,603,470 B2
(45) Date of Patent: Mar. 31, 2020

(54) MEDICAL SAFETY NEEDLE PREVENTIVE OF NEEDLEPOINT RE-EXPOSURE

(71) Applicant: MEDIKIT CO., LTD, Tokyo (JP)

(72) Inventors: Hiroaki Nakajima, Miyazaki (JP); Hirokazu Ando, Miyazaki (JP)

(73) Assignee: MEDIKIT CO., LTD, Tokyo (JP)

( * ) Notice: Subject to any disclaimer, the term of this patent is extended or adjusted under 35 U.S.C. 154(b) by 139 days.

(21) Appl. No.: 15/794,059

(22) Filed: Oct. 26, 2017

(65) Prior Publication Data

US 2018/0043137 A1 Feb. 15, 2018

Related U.S. Application Data

(63) Continuation of application No. 14/672,837, filed on Mar. 30, 2015, now Pat. No. 9,844,648, which is a
(Continued)

(51) Int. Cl.
*A61M 25/06* (2006.01)
*A61M 5/32* (2006.01)

(52) U.S. Cl.
CPC .......... *A61M 25/0631* (2013.01); *A61M 5/32* (2013.01); *A61M 5/321* (2013.01);
(Continued)

(58) Field of Classification Search
CPC .......... A61M 25/0612; A61M 25/0618; A61M 25/0625; A61M 25/0631; A61M 25/0693;
(Continued)

(56) References Cited

U.S. PATENT DOCUMENTS

| 5,447,501 A | 9/1995 | Karlsson et al. |
| 5,599,310 A | 2/1997 | Bogert |
| (Continued) | | |

FOREIGN PATENT DOCUMENTS

| CN | 1556717 | 12/2004 |
| CN | 1711115 | 12/2005 |
| (Continued) | | |

OTHER PUBLICATIONS

EPO Search Report in Patent Application No. 12886088.9, dated May 3, 2016.
(Continued)

*Primary Examiner* — Quynh-Nhu H. Vu
(74) *Attorney, Agent, or Firm* — Greenblum & Bernstein, P.L.C.

(57) ABSTRACT

A medical safety needle is comprised of a needle body having a needlepoint, a covering body having a detent portion slidable on the needle body to catch the needlepoint so as to cover the needlepoint, and a resilient cantilever supporting the detent portion, a sleeve following the covering body to cover a side face of the needle body, a collar portion slidably fitting on the covering body, which is configured to get in contact with the cantilever to press the cantilever radially inwardly, and a housing being formed in a unitary body with the collar portion or having an end face on which the collar portion is capable of being seated, the housing being configured to carry the covering body from a first position to have the needlepoint exposed to a second position to have the needlepoint covered by the covering body.

7 Claims, 13 Drawing Sheets

Related U.S. Application Data continuation of application No. PCT/JP2012/075972, filed on Oct. 5, 2012.

(52) U.S. Cl.
CPC ........... *A61M 5/322* (2013.01); *A61M 5/3273* (2013.01); *A61M 5/3275* (2013.01); *A61M 25/0618* (2013.01); *A61M 25/0693* (2013.01); *F04C 2270/0421* (2013.01)

(58) Field of Classification Search
CPC ...... A61M 5/1626; A61M 5/32; A61M 5/321; A61M 5/322; A61M 5/3273; A61M 5/327; A61B 50/3001
See application file for complete search history.

(56) References Cited

U.S. PATENT DOCUMENTS

| | | | | |
|---|---|---|---|---|
| 5,695,474 A | * | 12/1997 | Daugherty | A61M 5/3243 604/162 |
| 6,203,527 B1 | | 3/2001 | Zadini et al. | |
| 6,595,954 B1 | | 7/2003 | Luther | |
| 7,670,317 B2 | * | 3/2010 | Cindrich | A61M 5/158 604/167.01 |
| 8,006,675 B2 | | 8/2011 | Chyo | |
| 2003/0032927 A1 | | 2/2003 | Halseth et al. | |
| 2003/0036731 A1 | | 2/2003 | Wilkinson et al. | |
| 2003/0055385 A1 | | 3/2003 | Schooler et al. | |
| 2005/0027412 A1 | | 12/2005 | Wilkinson et al. | |
| 2008/0249478 A1 | * | 10/2008 | Ishikura | A61M 25/0618 604/198 |
| 2008/0249480 A1 | | 10/2008 | Riesenberger | |
| 2009/0281499 A1 | * | 11/2009 | Harding | A61M 25/0618 604/164.08 |
| 2009/0312711 A1 | * | 12/2009 | Brimhall | A61M 25/0618 604/164.08 |
| 2010/0222746 A1 | * | 9/2010 | Burkholz | A61M 25/0618 604/164.08 |

FOREIGN PATENT DOCUMENTS

| | | |
|---|---|---|
| CN | 101274116 | 10/2008 |
| JP | 2004-538104 | 12/2004 |
| JP | 2005-152282 | 6/2005 |
| JP | 2005-526526 | 9/2005 |
| WO | 92/18182 | 10/1992 |
| WO | 2003/013627 | 2/2003 |
| WO | 2003/015856 | 2/2003 |

OTHER PUBLICATIONS

Office Action issued in China Counterpart Patent Appl. No. 2012800762184, dated Oct. 28, 2016, along with an English translation thereof.

Office Action issued in China Counterpart Patent Appl. No. 2012800762184, dated Jan. 2, 2018, along with an English translation thereof.

* cited by examiner

MEDICAL SAFETY NEEDLE PREVENTIVE OF NEEDLEPOINT RE-EXPOSURE

CROSS-REFERENCE TO RELATED APPLICATIONS

This application is a continuation of U.S. application Ser. No. 14/672,837, filed Mar. 30, 2015, which is in turn a continuation of PCT International Application No. PCT/JP2012/075972 (filed Oct. 5, 2012), the entire contents of which are incorporated herein by reference.

BACKGROUND OF THE INVENTION

Field of the Invention

The present invention relates to a medical safety needle, and in particular relates to a medical safety needle preventive of re-exposure of its needlepoint after use.

Description of the Related Art

In order to introduce medicinal solution or a catheter into a patient's body, various needles for medical use have been used. After use, blood or any body fluid adheres on the needles for medical use and is sometimes contaminated with viruses such as HIV or hepatitis virus. The needles in medical use are potentially suspected to mediate infectious diseases.

There are proposed instruments in which needlepoints will be, after use, covered for the purpose of prevention of infection. U.S. Pat. Nos. 5,447,501, 5,599,310 and WO 92/18182 A1 disclose related arts.

SUMMARY OF THE INVENTION

Although the aforementioned related arts may not raise any problem in covering the needlepoints after use, risks are not sufficiently managed in light of some aspects, which means a needlepoint would be temporarily exposed in the process of covering the needlepoint and the needlepoint would covered may be re-exposed. The present invention has been achieved in view of this problem.

According to an aspect of the present invention, a medical safety needle is comprised of a needle body having a needlepoint; a covering body having a detent portion slidable on the needle body to catch the needlepoint so as to cover the needlepoint, and a resilient cantilever supporting the detent portion; a sleeve following the covering body to cover a side face of the needle body; a collar portion slidably fitting on the covering body, the covering body being configured to slide in the collar portion while the needlepoint is covered by the covering body, the collar portion being configured to get in contact with the cantilever to press the cantilever radially inwardly; and a housing being formed in a unitary body with the collar portion, the housing being configured to carry the covering body from a first position to have the needlepoint exposed to a second position to have the needlepoint covered by the covering body.

DETAILED DESCRIPTION OF THE EXEMPLARY EMBODIMENTS

Exemplary embodiments of the present invention will be described hereinafter with reference to the appended drawings. Medical safety needles according to these embodiments are available for the purpose of introducing a liquid such as a medicine or any tube such as a catheter into a patient's body. They are of course applicable not only to human beings but also to any creatures or articles. The embodiments described below are directed to examples for application as catheter introducers but not limited thereto. They are also applicable to blood collecting needles, indwelling needles or syringes, and further use of a catheter is not essential.

Throughout the following description and appended claims, an axial direction is defined and used as a direction of the needle when it pierces an object, and a radial direction is defined and used as a direction perpendicular thereto.

Figure 1:
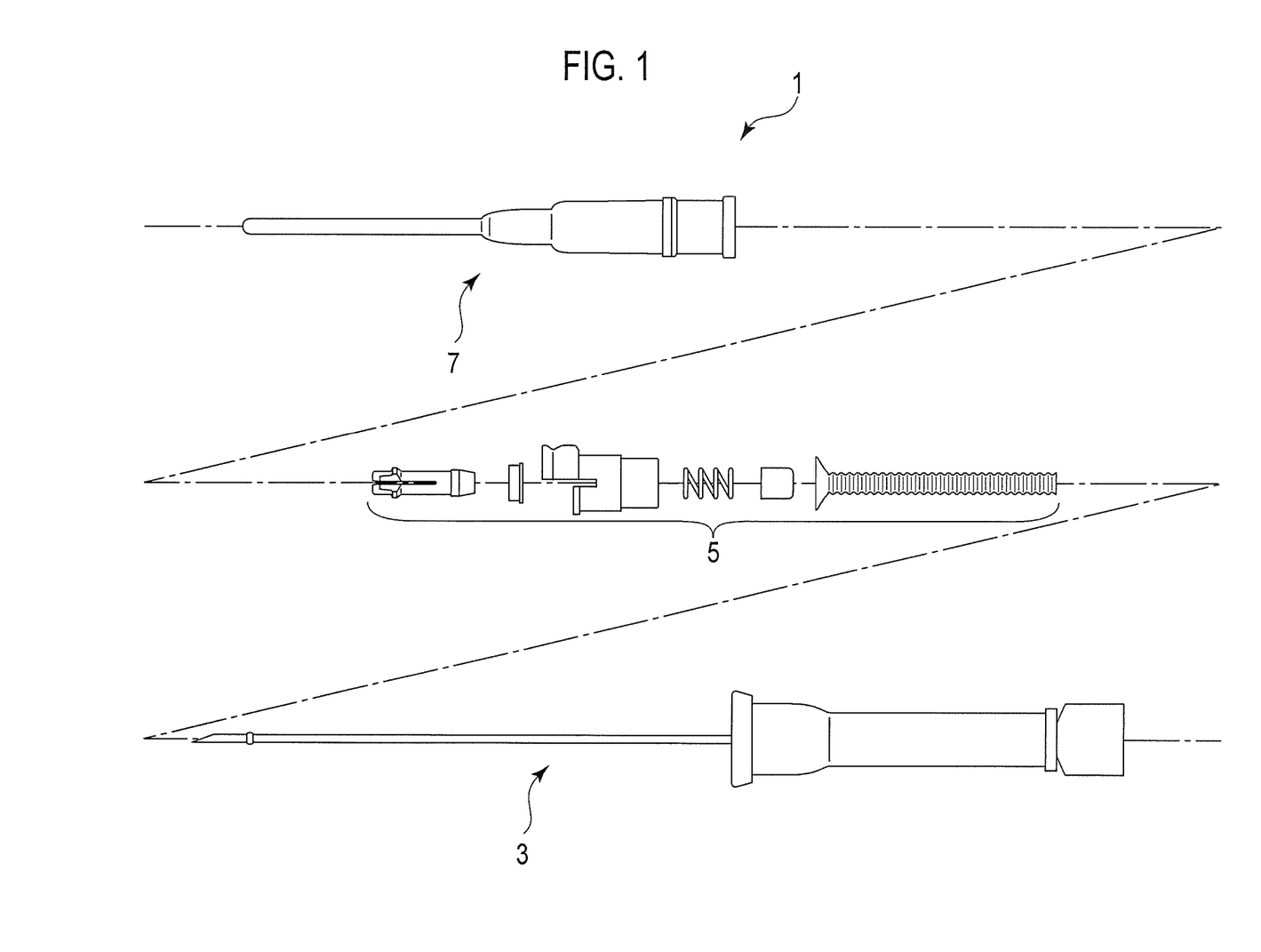
FIG. 1 is an exploded elevational view of a medical safety needle according to an embodiment of the present invention.
Figure 2A:
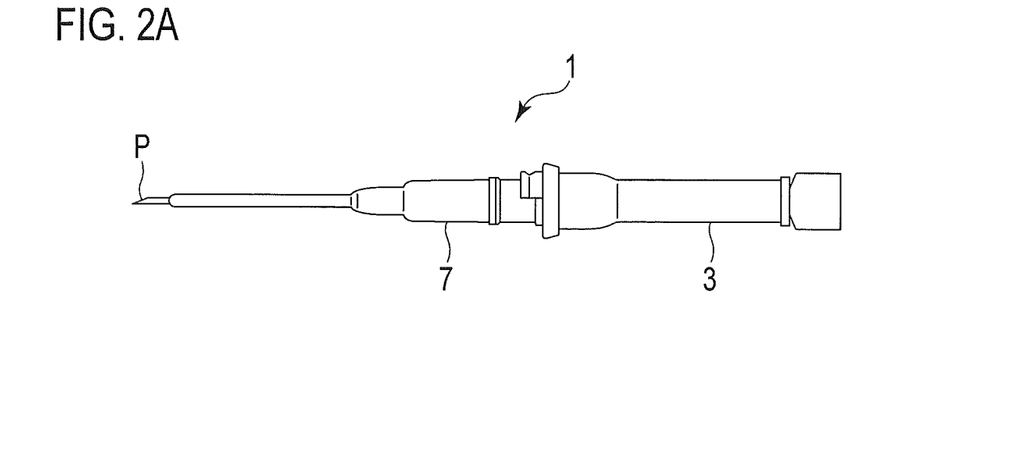
FIG. 2A is an elevational view of the medical safety needle, which shows an assembled state.

Referring to FIG. 1, a medical safety needle 1 according to an embodiment of the present invention is comprised of a needle 3 for piercing a patient's body, an assembly 5 including a covering body, and a catheter body 7 made to indwell in the patient's body after piercing. The assembly 5 fits with the needle 3 and the catheter body 7 further fits with them, thereby being assembled as shown in FIG. 2A and then used. Generally in the distribution process, a cover is attached thereto for covering a needlepoint P and the catheter body 7 but is not shown in FIG. 2A.

Figure 2B:
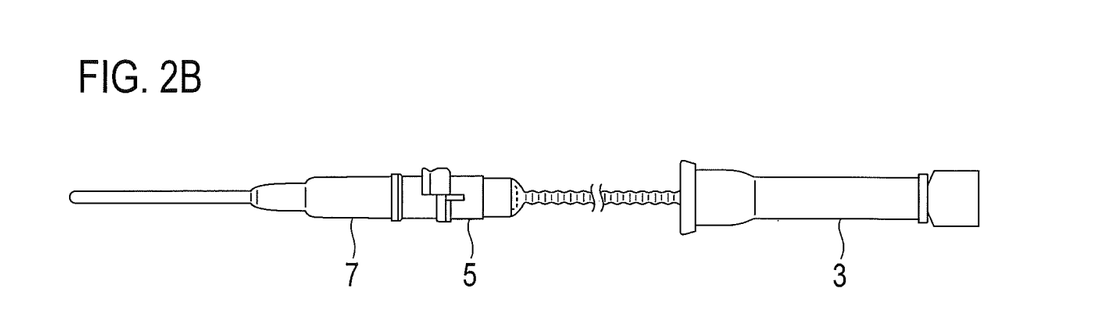
FIG. 2B is an elevational view of the medical safety needle, which shows a state where a covering body is extracted.

In the medical safety needle 1, as shown in FIG. 2A, the needlepoint P is slightly exposed out of the catheter body 7 and is used for piercing. After use, as the assembly including the covering body is extracted and gets in position to have the needlepoint P covered by the covering body as shown in FIG. 2B, its user or the patient is prevented from getting in contact with the needlepoint P. Before the covering body is extracted and then covers the needlepoint P, the catheter body 7 is barred from falling off.

Figure 2C:
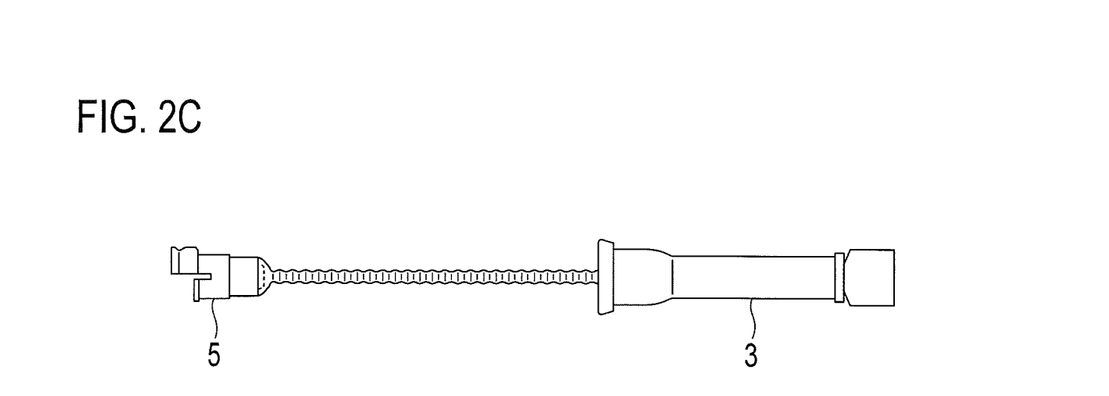
FIG. 2C is an elevational view of the medical safety needle, which shows a state where the covering body is extracted and thereafter a catheter body is detached.

After the covering body is extracted and then covers the needlepoint P, the catheter body 7 is made detachable as shown in FIG. 2C. Then the covering body catches the needlepoint P to prevent the needlepoint P from being re-exposed.

The medical safety needle 1 will be described in further detail hereinafter.

Figure 3:
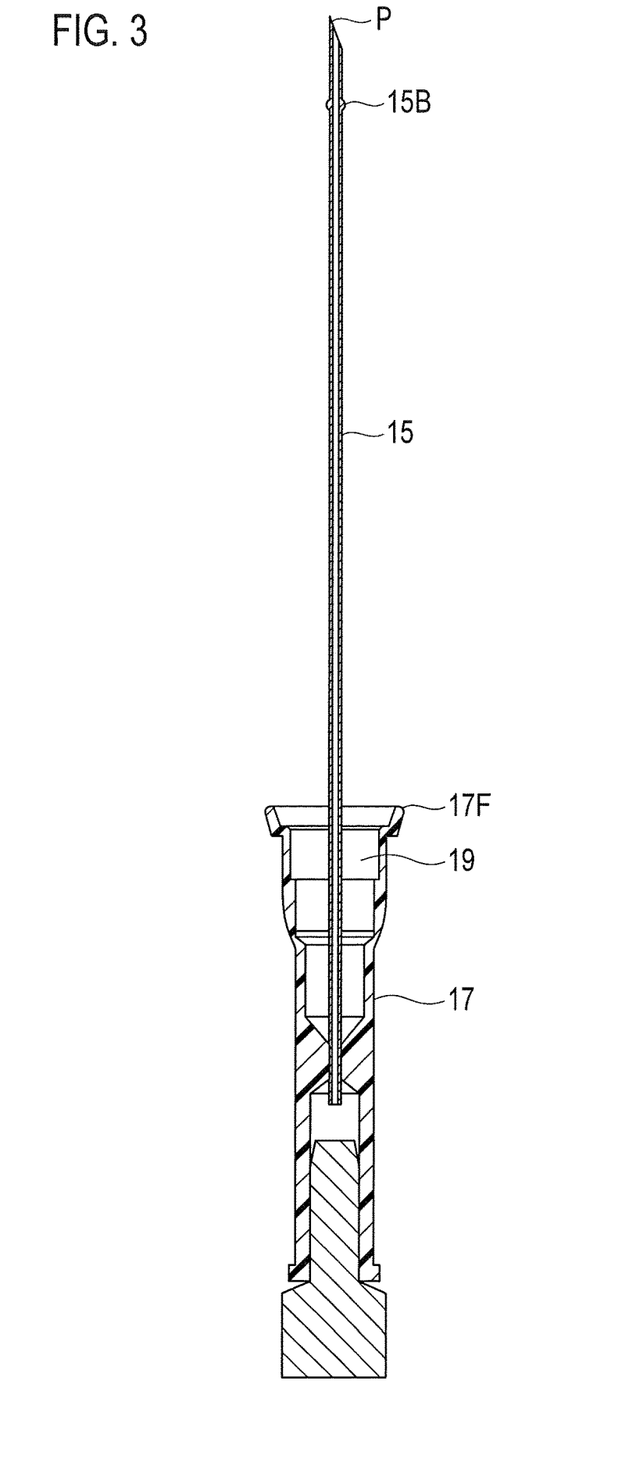
FIG. 3 is a sectional elevational view of a needle body and a handle.

Referring to FIG. 3 in combination with FIG. 1, the needle 3 is in general comprised of a needle body 15 and a handle 17 fixed therewith. Fixation may be made by any proper method such as press-fitting or glueing.

The needle body 15 is a needle for medical use and may be either tubular or solid. In a case where a tubular needle is applied thereto, blood that flashes back through the needle can be introduced into a rear end of the handle and this flash blood is applicable as an indicia for indicating that the needlepoint P is in place within a vein. Alternatively a through-hole may be provided on a side face of the needle body 15 in order to conduct the flash blood sideways.

Preferably a structure 15B for engaging with the covering body is provided at a proper position close to the needlepoint P. This structure 15B is any structure such as a bump (convex portion), a concave portion, both of them, or a step, which engages with the covering body when it slides on the covering body. This structure can be readily formed by locally pressing and collapsing the needle body 15 to some degree for example, but may be formed by any other method. The structure 15B is used to engage with and thereby operate the covering body, while its details will be described later.

A front end 17F of the handle 17, which is directed to the needlepoint P, is opened and formed therein is a cavity 19 so dimensioned as to house the assembly 5 therein. To allow access from the side into the cavity 19, an opening may be further provided on the side face of the handle 17. A rear end 17F of the handle 17, which is opposite to the needlepoint P, may be either opened or closed by any proper member. In a case where the flash blood is to be introduced therein, a chamber for keeping the blood may be formed therein.

Figure 4A:
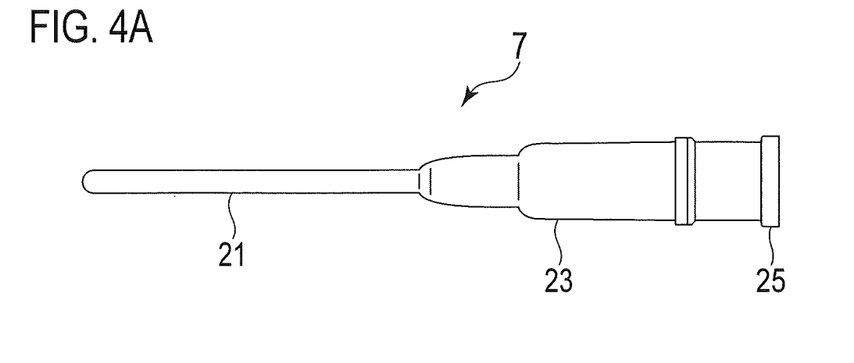
FIG. 4A is an elevational view of an exemplary catheter body, that is to be used in combination with the medical safety needle.

To the catheter body 7 applicable is a general indwelling catheter. Referring to FIG. 4A for example, the catheter body 7 is comprised of a flexible thin tube and a tapered body 23 larger in diameter. The interior of the tapered body 23 is a hollow in communication with the tube 21, which allows passage of infusion. In the hollow provided may be a valve for preventing back-flow of the infusion or the blood. A rear end of the tapered body 23 is comprised of a structure 25 for connection with an infusion circuit, a blood circuit, and a syringe, which generally includes a screw thread.

Figure 4B:
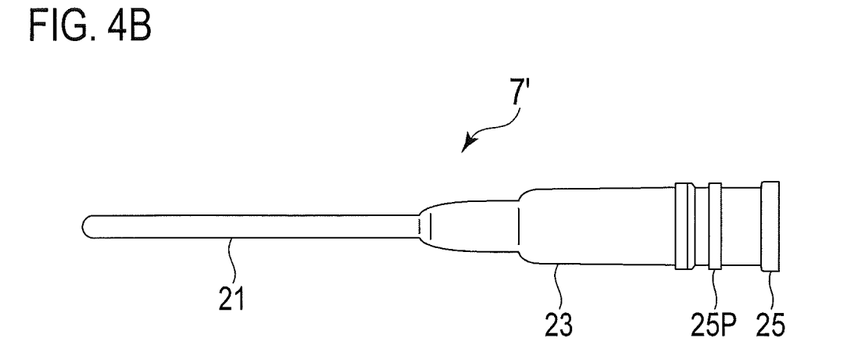
FIG. 4B is an elevational view of another exemplary catheter body.
Figure 4C:
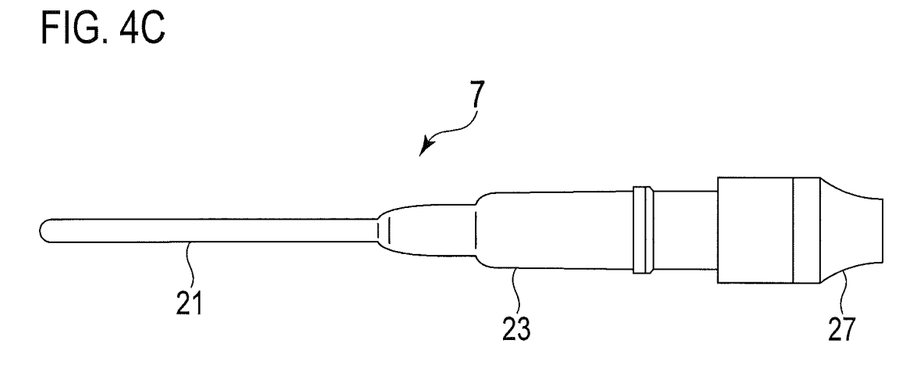
FIG. 4C is an elevational view of still another catheter body.
Figure 5A:
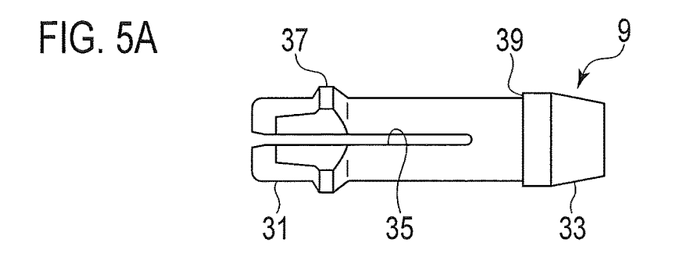
FIG. 5A is an elevational view of an exemplary covering body.
Figure 5B:
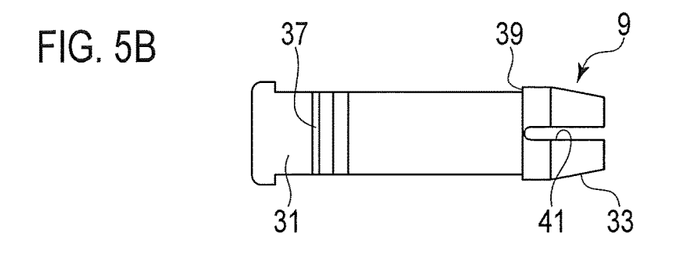
FIG. 5B is a plan view of the same.
Figure 5C:
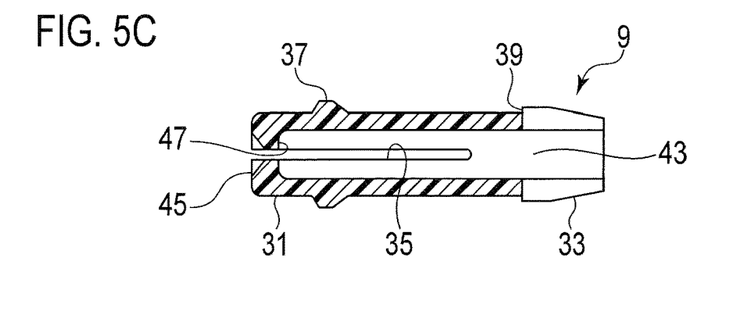
FIG. 5C is a sectional elevational view of the same.
Figure 5D:
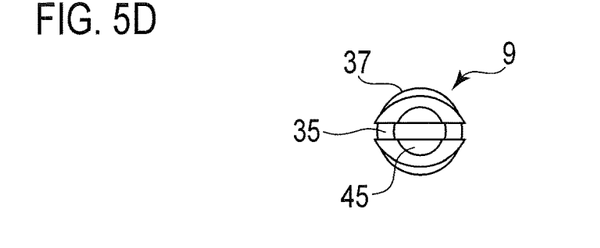
FIG. 5D is a side view of the same, which is viewed from an end opposed to the needlepoint.

Alternatively as shown in FIG. 4B a catheter body 7' having an auxiliary structure 25P for engagement may be applicable. The auxiliary structure 25P is, but not limited to of course, a circular projection for example. Still alternatively, the structure at the rear end of the catheter body 7 may include a rubber adapter 27 as shown in FIG. 4C.

Referring to FIGS. 5A through 8C in combination with FIG. 1, the assembly 5 includes a covering body 9 (or any of 9A through 9E) for covering the needlepoint P. The covering body 9 has a proper structure for fitting and sliding on the needle body 15.

In the examples shown in FIGS. 5A through 5D, the covering body 9 is of a substantially cylindrical shape and its interior is a hollow 43 so as to allow passage of the needle body 15. From its head portion 45 running longitudinally are slits 35 so that its upper and lower sections respectively form resilient cantilevers 31, thereby the head portion 45 is elastically openable and closable. The head portion 45 is formed to be concave like as a conical mortar, which guides insertion of the needle body 15. The cantilevers 31 are not limited to paired bodies but the number of them may be three or more, or a single cantilever as described later may be applicable. A rear end of the covering body 9 is in communication with the hollow 43 and thus open rearward, thereby the needle body 15 can get through the covering body 9 from its rear end to the head portion 45.

At the side face of the covering body 9, and also on the cantilevers 31, formed are jaw portions 37 for getting contact with a collar described later. The jaw portions 37 are, although not limited to, annular and projecting radially outward and are, as shown in the drawings, formed as projections respectively having slopes. Such a shape is advantageous in reduction of friction when it is retracted into a collar portion 13, because of the slopes. This is further advantageous in smooth retraction of the covering body 9 into the collar portion 13 even without assistance by an elastic body 81 described later. Further a portion of the covering body 9, on the side face and close to the rear end, has a step 39 so as to latch on an engaging body 53 described later.

The rear end of the covering body 9 preferably has slits 41 so as to have elasticity. The slits 35 and the slits 41 are circumferentially deviated at 90 degrees for example.

Figure 11A:
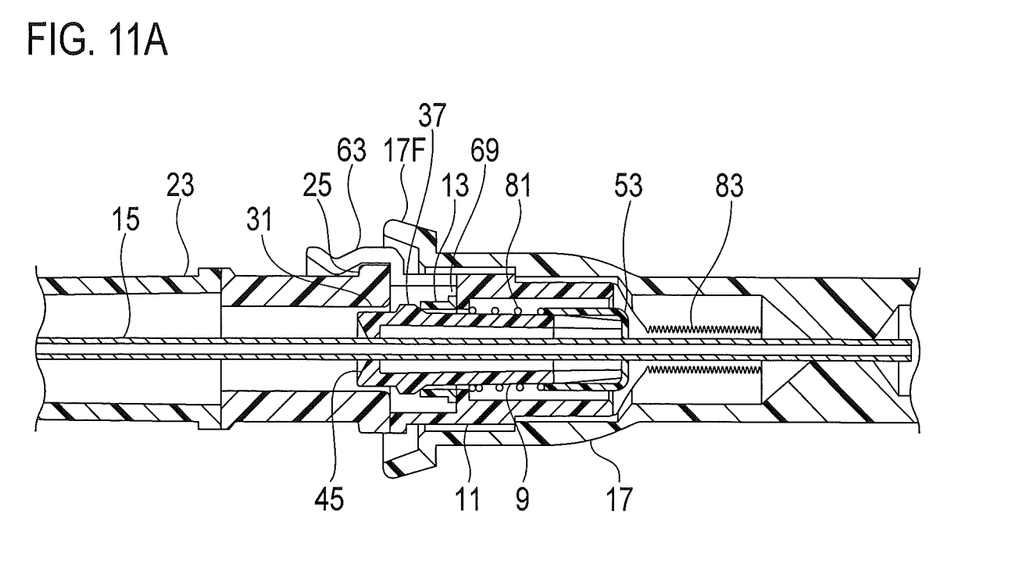
FIG. 11A is a partial sectional view of the medical safety needle, which shows a state where a rear end structure of the catheter body is pinched between a housing and a top end of the covering body so as not to fall off.
Figure 13A:
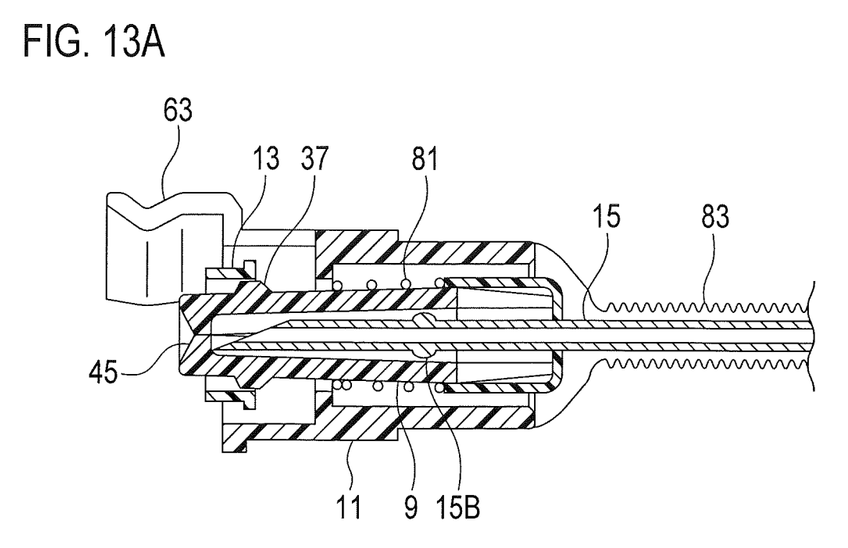
FIG. 13A is a partial sectional view of the medical safety needle, which shows a state where the covering body catches the needlepoint to prevent the needlepoint from being re-exposed.
Figure 13B:
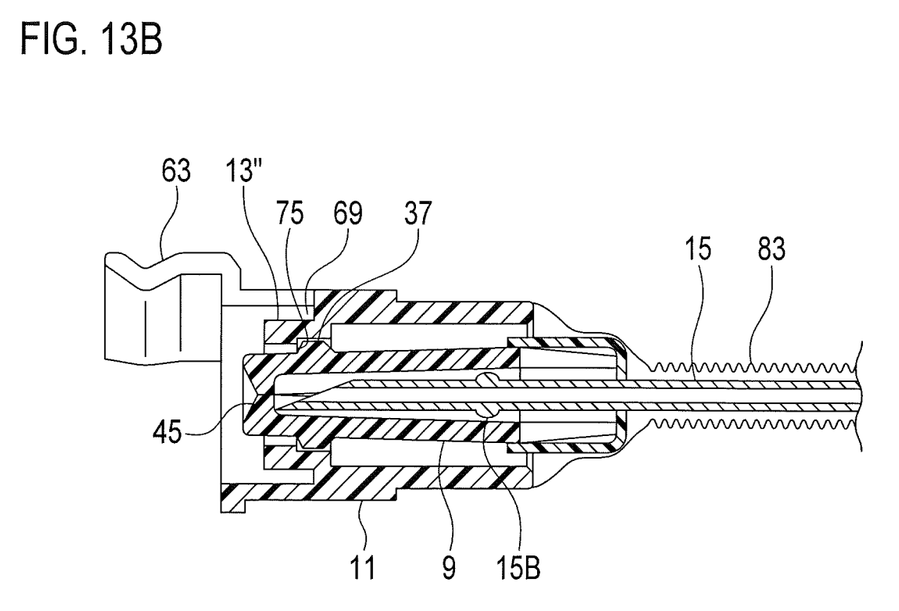
FIG. 13B is a partial sectional view of the medical safety needle according to another example, which shows a state where the covering body catches the needlepoint to prevent the needlepoint from being re-exposed.

Each cantilever 31, at its top end for example, supports a detent portion 47 that projects radially inward like as a hook. The detent portions 47 slidably get in contact with the needle body 15 as shown in FIG. 11A, and, when the needlepoint P is retracted therein, cover the needlepoint P and are capable of catching the needlepoint P as shown in FIGS. 13A, 13B. Alternatively the detent portions 47 may be, in an initial state, not in contact with the needlepoint.

Figure 6A:
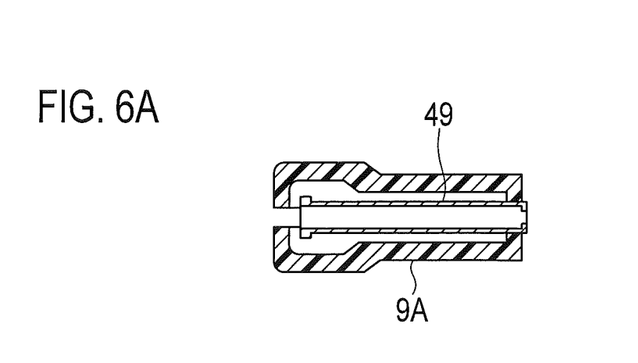
FIG. 6A is a sectional elevational view of another exemplary covering body.

According to another example shown in FIG. 6A, the covering body 9A is comprised of a sleeve 49 extensibly housed therein, thereby being telescopically extensible and contractible. The sleeve 49 at its rear end has an inward projection for engaging with the structure 15B of the needle body 15. Such an extensible-contractible structure is advantageous in reduction in size of the covering body 9A. Further, in a state where the sleeve 49 is housed in the covering body 9A, its front end may be elongated so as to fit in the interior of the cantilever at its front end and in its internal periphery. As the needle body 15 does not get in contact with the cantilever, the needle body 15 can slide under a very small frictional resistance independent of the diameter of the needle body 15.

Figure 6B:
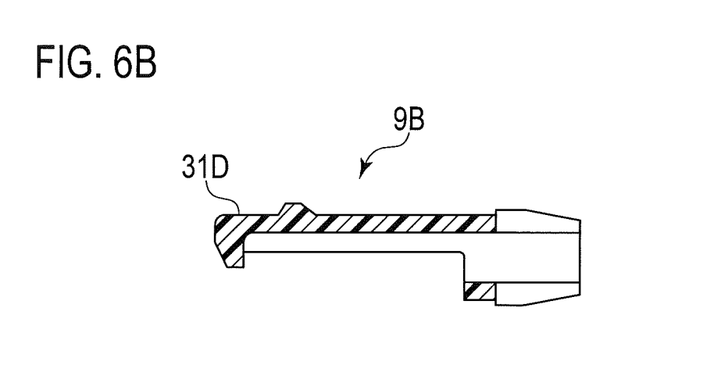
FIG. 6B is a sectional elevational view of the other exemplary covering body.
Figure 6C:
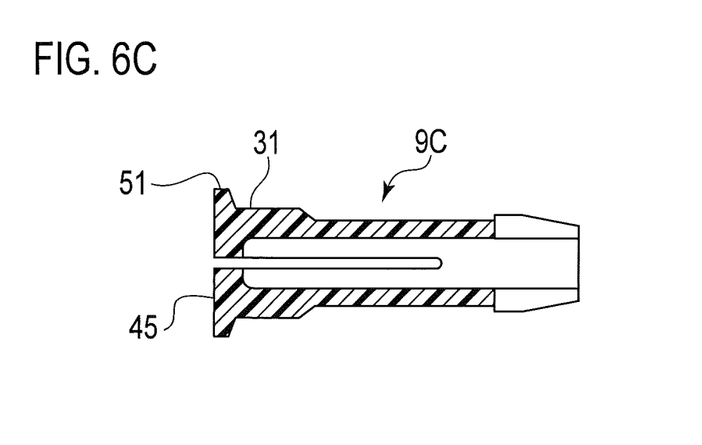
FIG. 6C is a sectional elevational view of still another covering body.

According to the other example shown in FIG. 6B, the covering body 9B does not have the slits 35 and therefore has a single cantilever 31A. Such a structure is also applicable as long as its detent portion 47 is sufficient to cover and catch the needlepoint P.

Figure 11B:
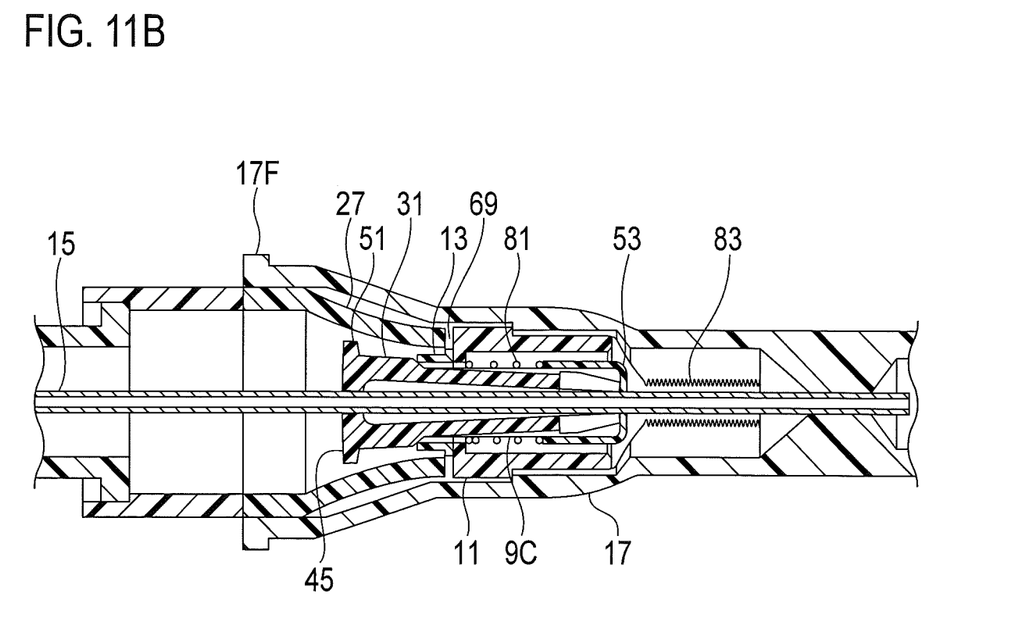
FIG. 11B is a partial sectional view of a medical safety needle according to another example, which shows a state where a rear end structure of the catheter body is pinched between a housing and a top end of the covering body so as not to fall off.

In any of these embodiments, further, any proper shape adapted to the proximal end structure of the catheter body 7 may be applied to vicinities of the front end of the covering body. In the example shown in FIG. 6C for example, the vicinity of the front end of the covering body 9C is comprised of a flange-like section 51 projecting radially outward, and this is advantageous in prevention of the catheter body 7 with a rubber adapter from falling off as shown in FIG. 11B, while its details will be described later.

In any of these embodiments, to a material for the covering body applicable is polyoxymethylene (POM), polyetheretherketone (PEEK), high density polyethylene (HDPE), polyamide (PA), polycarbonate (PC), polyethylene terephthalate (PET), polyvinyl chloride (PVC), low density polyethylene (LDPE) or such. These are advantageous in creation of sufficient strength and elasticity in the covering body.

Figure 7:
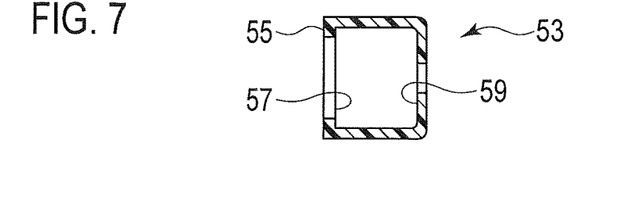
FIG. 7 is a sectional elevational view of an exemplary engaging body, that is to be used in combination with the covering body.
Figure 8A:
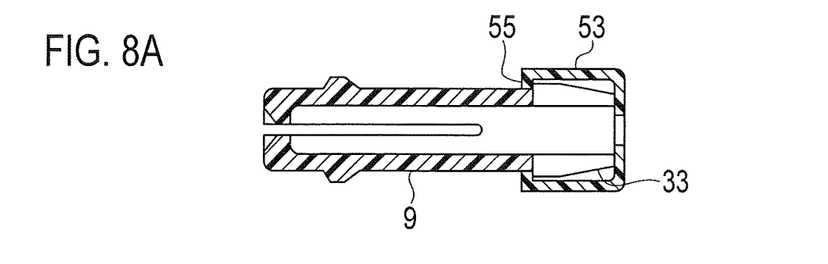
FIG. 8A is a sectional elevational view of an exemplary covering body combined with the engaging body.
Figure 12A:
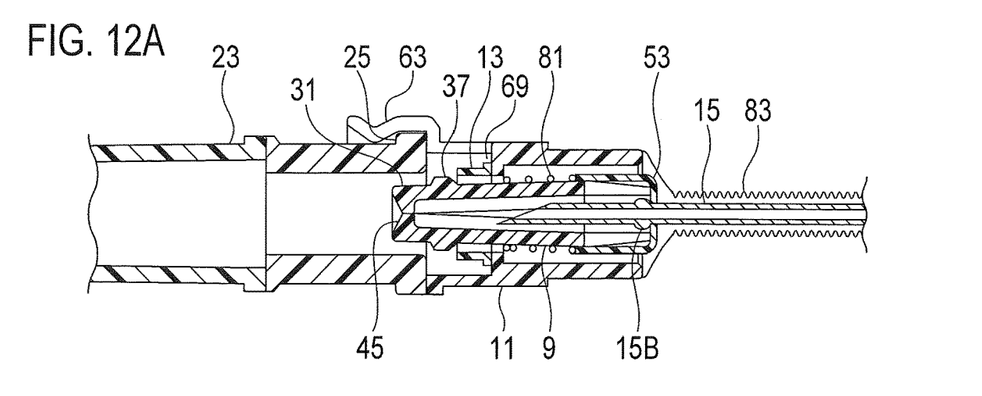
FIG. 12A is a partial sectional view of the medical safety needle, which shows a state where the needlepoint is retracted in the covering body.

Referring to FIG. 7, the covering body according to any of the embodiments is preferably comprised of an engaging body 53. The engaging body 53 is formed substantially in a cylindrical shape. A front end thereof has a face 55 on which an elastic body 81 described later is seated on, and a rear end thereof properly shrinks in diameter so as to allow passage of the needle body 15 but engage with its structure 15B. The engaging body 53, by an internal face 59 at its front end, as shown in FIG. 8A, engages with the step 39 of the covering body and, by an internal face 59 at its rear end, as shown in FIG. 12A for example, engages with the structure 15B of the needle body 15.

Figure 8B:
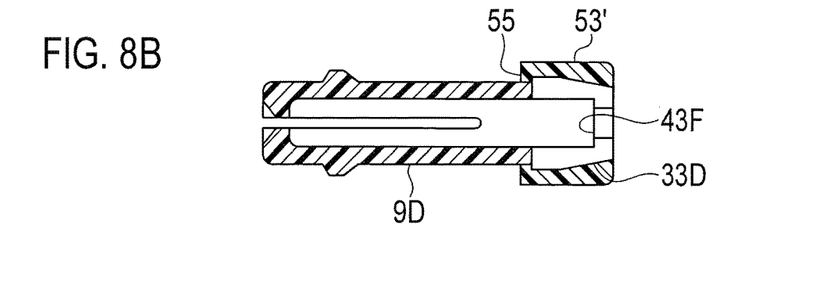
FIG. 8B is a sectional elevational view of another exemplary covering body combined with the engaging body.
Figure 8C:
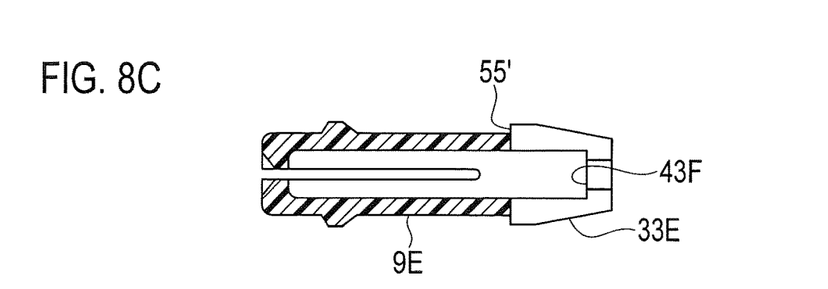
FIG. 8C is a sectional elevational view of an exemplary covering body as a unitary body with the engaging body.
Figure 9A:
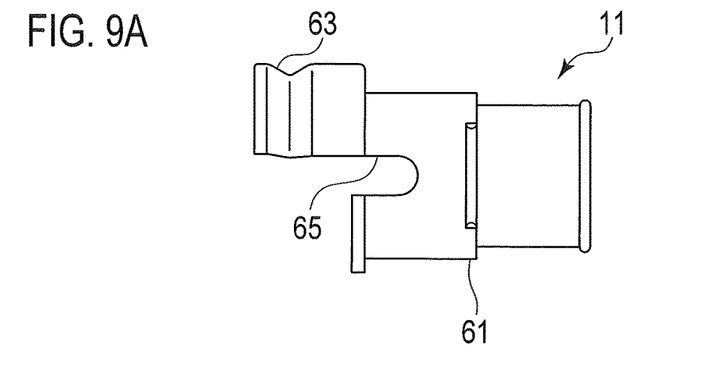
FIG. 9A is an elevational view of an exemplary housing.
Figure 9B:
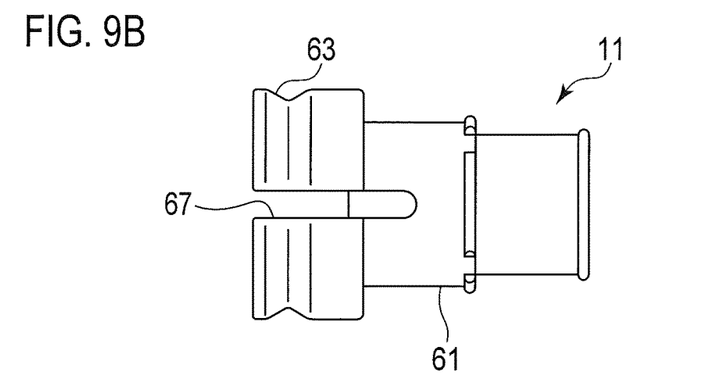
FIG. 9B is a plan view of the same.
Figure 9C:
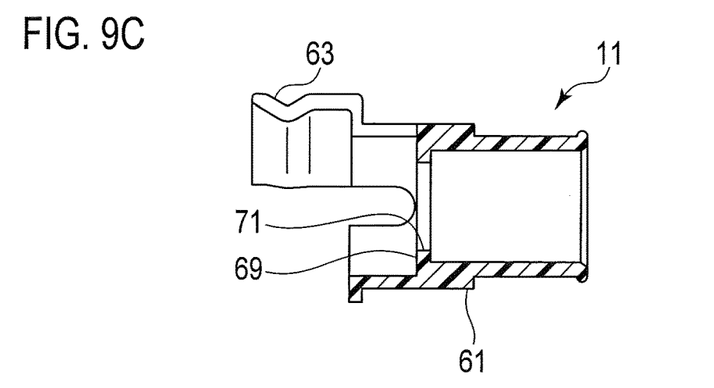
FIG. 9C is a sectional elevational view of the same.
Figure 9D:
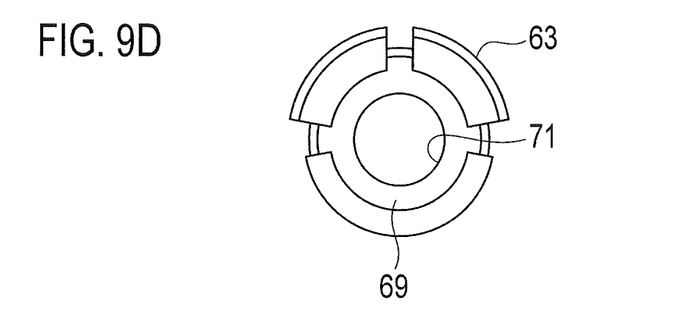
FIG. 9D is a side view of the same, which is viewed from an end opposed to the needlepoint.

Engagement with the structure 15B of the needle body 15 may be alternatively established by a rear end face 43F of a covering body 9D of itself as shown in FIG. 8B. In this case, a rear end of an engaging body 53' may not cover the rear end of the covering body 9D. Still alternatively, a covering body 9E by itself may function as a stopper as shown in FIG. 8C. In this case, a step 55' of the covering body 9E projects radially outward relatively to the great extent and the elastic body 81 is seated thereon.

Still alternatively, a washer or any other intervening body may be used for the purpose of engagement with the structure 15B. The washer or such may be put in between the covering body and the stopper or may fit in the interior of the covering body or the stopper.

Further any of the aforementioned covering bodies may be, in the interior or at either the front end or the rear end, comprised of a water-absorbent consisting of surgical cotton or a water-absorbing polymer.

Referring to FIGS. 9A through 10B in combination with FIG. 1, the assembly 5 includes a housing 11 that houses the covering 9 (any of 9A through 9E). The housing 11 has a shape adapted for being housed in the handle 17, so that its user is unlikely to directly get in touch therewith. Alternatively, it may be modified so that the flange 63 is considerably elongated forward so as to allow the user to pick and move it by fingers. The housing 11, as described later, engages with and moves along with the catheter body 7, and, in the process of the movement, carries the covering body 9 (any of 9A through 9E) toward the needlepoint P and makes it cover the needlepoint P.

In any of the examples shown in FIGS. 9A through 9D for example, the housing 11 is formed substantially in a cylindrical shape and its outer shell 61 has a shape adapted for fitting in and being seated on the cavity 19 of the handle 17. A flange 63 extending forward and radially outward from the outer shell 61 is bent in a hook-like shape so as to engage with the rear end structure 25 (or 25P) of the catheter body 7. In order to create elasticity in the flange 63, the outer shell 61 may have slits 65, 67. The elasticity of the flange 63 makes the catheter 7 easy to engage with and disengage from it. Either or both of the flange 63 and its rear end structure 25 (or 25P) may have any structures for assisting engagement.

The housing 11 in the interior has a radially inward projection to form an end face 69 at its front and an opening 71 therein respectively. The collar portion 13 is seated on the end face 69 and the covering body 9 (or any of 9A through 9E) fits in the opening 71.

Figure 10A:
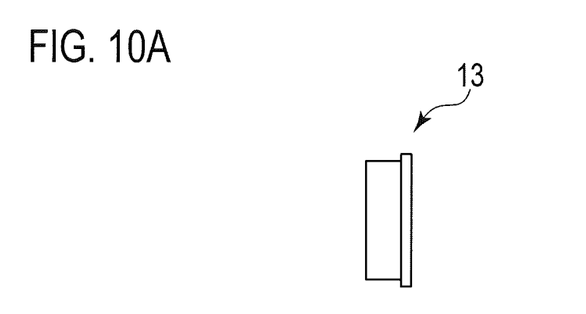
FIG. 10A is an elevational view of an exemplary collar portion.

Referring to FIG. 10A, the collar portion 13 is of a ring-like shape, but may be, as being cut out therefrom in part, of a C-letter shape. To a material for the collar portion 13 applicable is any metal for example, and exemplified are stainless steels such as ISO/TS155101-No. 6 (JIS SUS304), ISO/TS155101-No. 67 (JIS SUS430) and a general cold-rolled steel (JIS SPCC), but not limited thereto. Because a material with a high specific elastic modulus such as a metal sounds a loud clicking noise when the head portion of the covering body 9 closes, it is advantageous in informing the user of that its operation is securely finished.

Figure 10B:
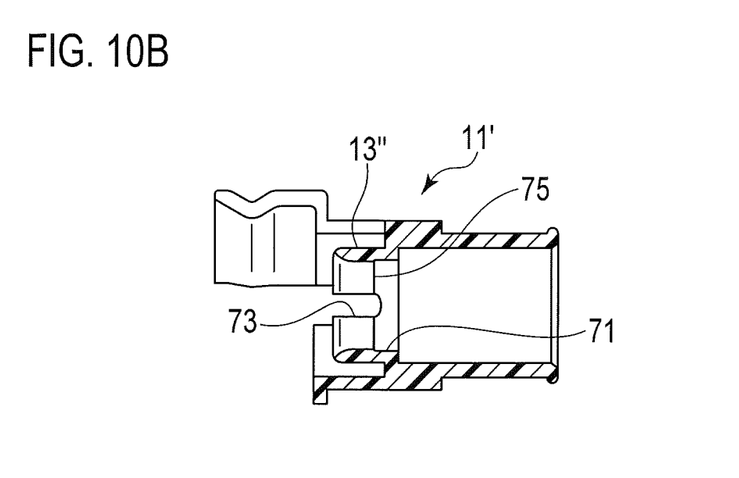
FIG. 10B is a sectional elevational view of an exemplary collar portion as a unitary body with the housing.

Further as shown in FIG. 10B, the collar portion 13" may be of a unitary body with the housing 11'. In this case, in order to create elasticity in the collar portion 13", slits 73 may be formed. Further the internal periphery of the collar portion 13 or 13" may have a step 75 that engages with the covering body 9 (or any of 9A through 9E), which is advantageous in prevention of the covering body 9 (or any of 9A through 9E) from projecting out as shown in FIG. 13B.

Referring to FIGS. 11A, 11B in combination with FIG. 1, the assembly 5 may further includes an elastic body repulsively interposed between the housing 11 (or 11') and the covering body 9 (or any of 9A through 9E), and an extensible and contractible sleeve 83 surrounding the needle body 15. To the elastic body 81 applicable is a coil spring for example.

As the elastic body 81 intervenes, the covering body 9 (or any of 9A through 9E) is biased backward and then the jaw portions 37 on the cantilevers 31 abut on the collar portion 13, thereby biasing the cantilevers 31 radially inward as shown in FIG. 13A. This assists the covering body 9 in smoothly retracting into the collar portion 13 and is advantageous in prevention of the needlepoint P from being re-exposed after the needlepoint P is retracted in the covering body 9. Alternatively the bias may be made not by the repulsive force by the elastic body 81 but by repulsive force of the cantilever 31 by itself, or further alternatively may be made by a C-ring or a coil spring of any elastic material such as rubber or metal wound around the cantilever 31. Further in this case, the collar portion 13 and the elastic body 81 may be made in a unitary body.

The sleeve 83 may be a bellows for example or any telescopic nested structure for the purpose of extension and contraction, but is not limited thereto. A top end of the sleeve 83 is fixed to an outer periphery or a rear end of the housing 11 (or 11'), or, if possible, to the rear end of the engaging body 53. A rear end thereof is fixed to any part of the handle 17 or any part of the needle body 15. Fixation may be made by glueing or any other proper means. The sleeve 83, when the covering body 9 (or any of 9A through 9E) is extracted, follows it and is therefore elongated, thereby covering the side face of the needle body 15 as shown in FIG. 2C.

Referring to FIG. 11A, the respective members as described above are assembled in a way as described below. More specifically, the needle body 15 passes through the covering body 9 (or any of 9A through 9E) and the covering body 9 (or any of 9A through 9E) is housed in the housing 11 (or 11') in a state where its head 45 projects out of the end face 69 toward the needlepoint P. The collar portion 13 (or 13') slidably fits on the cantilevers 31 and, when abutting on the jaw portions 37, biases the detent portions 47 radially inward. The elastic body 81, when applied, repulsively intervenes between the housing 11 (or 11') and the covering body 9 (or any of 9A through 9E). The covering body 9 (or any of 9A through 9E) and the housing 11 (or 11') are housed in the cavity 19 of the handle 17. At the back thereof, in the cavity 19 housed is the sleeve 83 in a state of being compressed. The flange 63 elongated from the housing 11 (or 11') is exposed ahead of the flange 17F of the handle 17 so as to engage with the rear end structure 25 of the catheter 7.

The head portion 45 of the covering body 9 (or any of 9A through 9E), in a state of being assembled, sufficiently projects forward from the end face 69 and the rear end structure 25 of the catheter body 7 is pinched between the head portion 45 and the flange 63, thereby being prevented from falling off.

In a case where the rubber adapter 27 is provided at the rear end of the catheter body 7, as shown in FIG. 1B, the handle 17 may have a flange 17F so elongated as to correspond therewith and the rear end structure 25 of the catheter body 7 may be pinched between the head portion 45 and the flange 17F. In order to prevent displacement, the covering body 9C having the flange-like section 51 is preferably used. This embodiment also successfully prevents the catheter body 7 from falling off.

Referring again to FIG. 1, assembly of the medical safety needle 1 can be carried out in the following way for example.

The collar portion 13 for example is seated on the housing 11 and the covering body 9 is inserted from the side of the collar portion 13. From the opposite side relative to the collar portion 13, the coil spring 81 is inserted into the housing 11 and, while compressing the coil spring 81 compressed, the engaging body 53 is combined with the covering body 9. If necessary, the front and rear ends of the sleeve 83 are adhered to the housing 11 and the handle 17 respectively. By doing so, the assembly 5 is finished. From the head portion 45 of the covering body 9, the needle body 15 is passed through and its rear end is fixed to the handle 17. By doing so, the needle 3 is finished. The catheter body 7 is fit on the needle 3 and its rear end structure 25 is pressed in between the covering body 9 and the flange 63. By housing the assembly 5 along with the catheter body 7 into the cavity 19 of the handle 17, the medical safety needle 1 is finished. Even in a case where any of its members are those according to any of the modified examples, assembly can be carried out in substantially the same way.

According to the medical safety needle 1 as described above, action to cover the needlepoint P after use and action of the medical safety needle 1 will be described below.

Figure 14A:
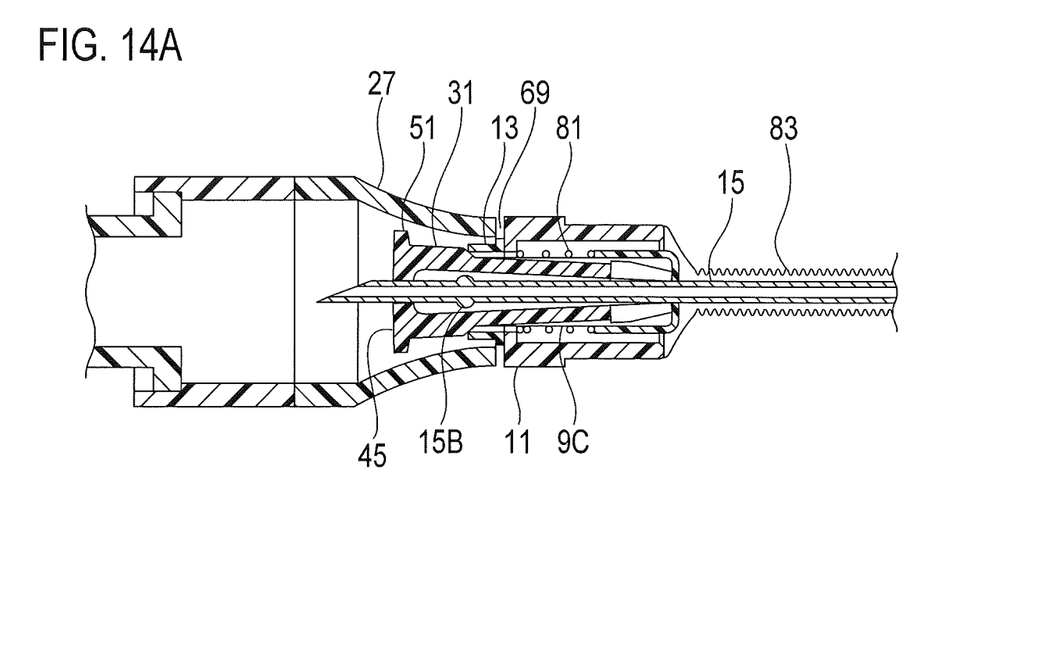
FIG. 14A is a partial sectional view of the medical safety needle according to the example shown in FIG. 11B, which shows a process in which the needlepoint is retracted in the covering body.

The medical safety needle 1 is served and put into use in a state as shown in FIG. 2A. The needle body 15 is, as shown in FIGS. 11A, 11B, extracted forward out of the covering body 9 and the needlepoint P is exposed out of the top end of the catheter body 7. In this state, the needlepoint P along with the catheter body 7 is made to pierce the patient, and, when the top end of the catheter body 7 is positioned in place within the vein of the patient, the handle 17 is taken back with leaving the catheter body 7 there as shown in FIG. 2B. Then the assembly 5 is extracted from the handle 17. The rear end structure 25 of the catheter body 7 even then keeps engaging with the flange 63 and being pinched between the covering body 9 and the flange 63. Or as shown in FIG. 14A, the flange-like section 51 keeps projecting radially outward. Therefore the catheter body 7 does not fall off.

Figure 12B:
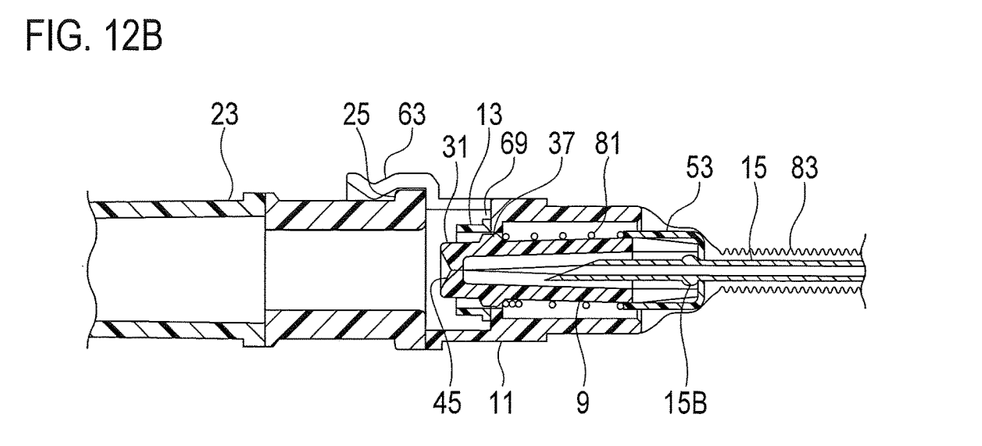
FIG. 12B is a partial sectional view of the medical safety needle, which shows a state where the covering body is also retracted in the collar portion.
Figure 12C:
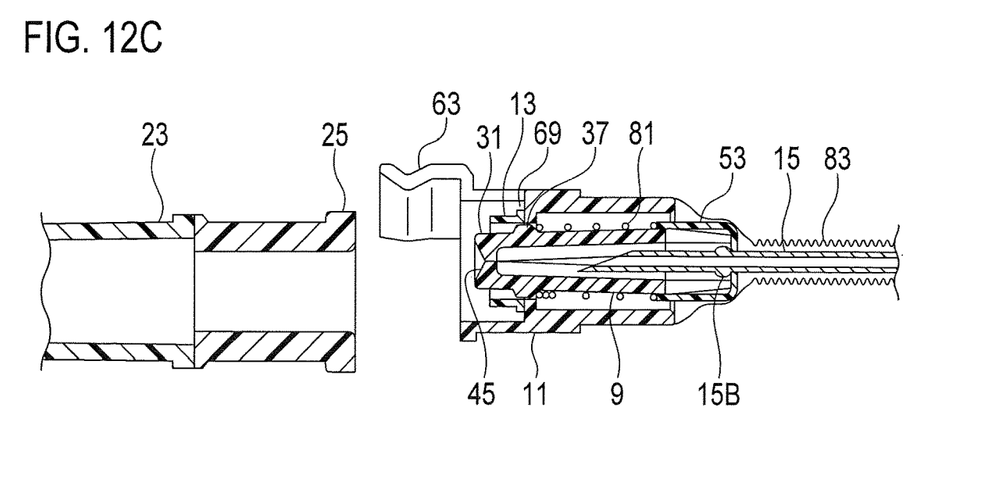
FIG. 12C is a partial sectional view of the medical safety needle, which shows a state where the catheter body is detached from the housing.
Figure 14B:
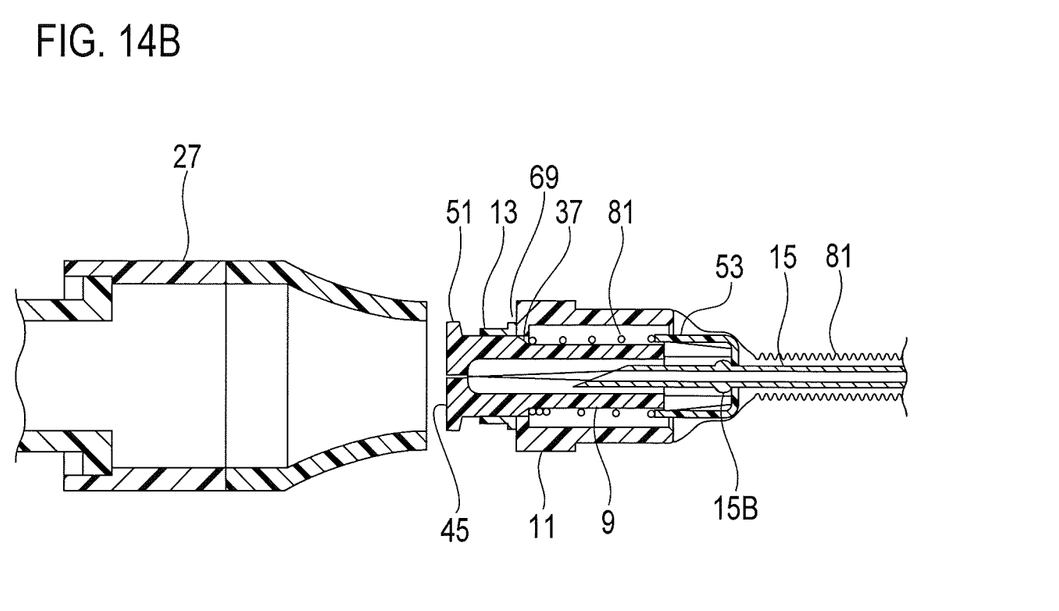
FIG. 14B is a partial sectional view of the medical safety needle according to the example shown in FIG. 11B, which shows a state where the needlepoint is retracted in the covering body and then the catheter body is detached therefrom.

As the handle 17 is further taken back, the needlepoint P is retracted into the covering body 9, the head portion 45 of the covering body 9 closes, then the covering body 9 is allowed to get into the interior of the collar portion 13. Next, as the structure 15B of the needle body 15 gets engaged with the engaging body 53, the covering body 9 gets prevented from falling off from the needle body 15 and the covering body 9 is retracted into the collar portion 13 as shown in FIGS. 12B, 14B. As being pressed thereby, the head portion and the flange-like section 51 get prevented from re-opening. As the interference by the covering body 9 is gone, the catheter 7 gets allowed to be detached as shown in FIGS. 12C, 14B and 2C.

Because the needlepoint P is thus covered by the covering body 9 as shown in FIG. 2C, the user and the patient are prevented from unintentionally getting in touch with the needlepoint P. If someone tried to re-expose the needlepoint P, the detent portions 47 would catch the needlepoint P as shown in FIG. 13A so as to prevent the needlepoint P from being re-exposed. Then the collar portion 13 follows the covering body 9 and presses the cantilever 31 so as to keep the detent portions 47 catching the needlepoint P, thereby re-exposure of the needlepoint P is reliably prevented. In a case where the housing 11 has the step 75, it engages with the covering body 9 and is thereby barred from moving forward. Re-exposure of the needlepoint P is also reliably prevented.

In the process as described above, before ensuring coverage of the needlepoint P, the catheter body 7 is prevented from being detached. Therefore, as either the catheter body 7 or the covering body 9 consistently covers the needlepoint P except the case of piercing, the needlepoint P will be never exposed even as a transitory event. The user is not required to pay particular attention to disposal of the needlepoint P when he or she is required to pay sufficient attention to the procedure for connecting the catheter body 7 to an infusion system for example.

Although the invention has been described above by reference to certain embodiments of the invention, the invention is not limited to the embodiments described above. Modifications and variations of the embodiments described above will occur to those skilled in the art, in light of the above teachings.

INDUSTRIAL APPLICABILITY

The invention provides a medical safety needle capable of preventing re-exposure of a covered needlepoint is provided.

What is claimed is:

1. A medical safety needle, comprising:
   a needle body having a needlepoint;
   a covering body having a detent portion slidable on the needle body to catch the needlepoint so as to cover the needlepoint, and a resilient cantilever supporting the detent portion;
   a sleeve following the covering body to cover a side face of the needle body;
   a collar portion slidably fitting on the covering body, the covering body being configured to slide in the collar portion while the needlepoint is covered by the covering body, the collar portion being configured to get in contact with the cantilever to press the cantilever radially inwardly, the collar portion having one of a ring-like or a C-letter shape; and
   a housing being formed in a unitary body with the collar portion, the housing being configured to carry the covering body from a first position to have the needlepoint exposed to a second position to have the needlepoint covered by the covering body.

2. The medical safety needle of claim 1, wherein the cantilever has a jaw portion in contact with the collar portion so that the collar portion presses the cantilever via the jaw portion.

3. The medical safety needle of claim 1, further comprising:
   a catheter body having a proximal end structure to fit on the needle body,
   wherein the housing has a flange portion capable of engaging with the proximal end structure.

4. The medical safety needle of claim 3, further comprising:
   a handle supporting the needle body and having a cavity so dimensioned as to house the covering body and the housing.

5. The medical safety needle of claim 4, wherein the covering body, the housing and the handle are so dimensioned as to have the covering body projected out of the end face toward the needlepoint, when the covering body is at the first position, so as to prevent the proximal end structure from displacing from between the projected covering body and the flange portion.

6. The medical safety needle of claim 1, further comprising:
   an elastic body repulsively interposed between the housing and the covering body so as to bias the cantilever in a direction where the detent portion is made to catch the needlepoint.

7. The medical safety needle of claim 1, wherein the needle body has one or more structures selected from the group consisting of a convex portion, a concave portion and a step, the structures being engageable with the covering body.

* * * * *